Figure 3:
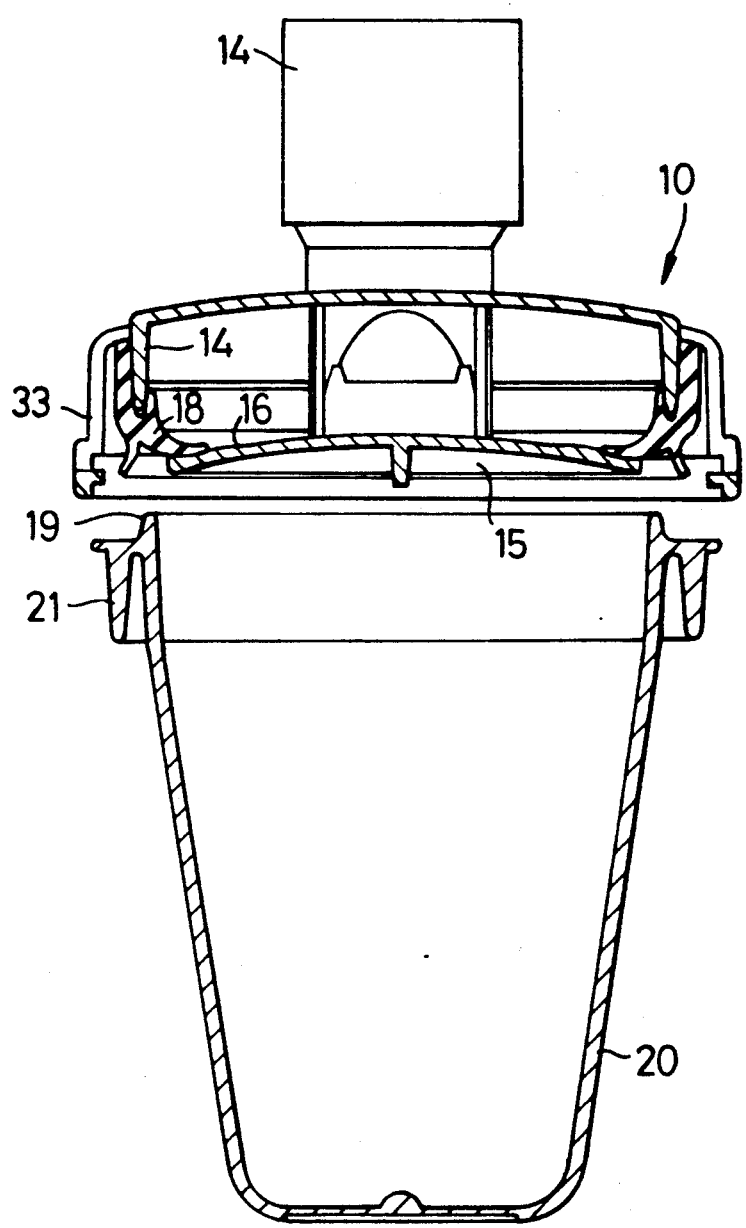

United States Patent [19]

Hicks

[11] Patent Number: 5,168,868
[45] Date of Patent: Dec. 8, 1992

[54] WATER TRAP FOR RESPIRATORY AIRLINE

[75] Inventor: Richard B. Hicks, Kingston-upon-Thames, United Kingdom

[73] Assignee: Intersurgical Limited, Twickenham, United Kingdom

[21] Appl. No.: 707,005

[22] Filed: May 29, 1991

[30] Foreign Application Priority Data

Jun. 8, 1990 [GB] United Kingdom ............... 9012881

[51] Int. Cl.$^5$ .................. A62B 7/10; A62B 19/00; A62B 23/02; A62B 9/02
[52] U.S. Cl. .................. 128/205.12; 128/205.24; 604/284; 604/319; 604/322
[58] Field of Search .................. 128/204.18, 205.12, 128/205.24, 912; 604/284, 317, 319–326

[56] References Cited

U.S. PATENT DOCUMENTS 3,968,812  7/1976  Eross .................. 137/188
4,457,305  7/1984  Shanks et al. .................. 128/205.12
4,867,153  9/1989  Lorenzen et al. .................. 128/205.12
4,951,661  8/1990  Sladek .................. 128/202.27

FOREIGN PATENT DOCUMENTS 8603169  11/1987  Fed. Rep. of Germany .
3742888   7/1989  Fed. Rep. of Germany .
1456570  11/1976  United Kingdom .......... 128/204.18

Primary Examiner—David A. Wiecking
Assistant Examiner—Kimberly L. Asher
Attorney, Agent, or Firm—Young & Thompson

[57] ABSTRACT

A water trap for a respiratory airline comprises a top and base the respective openings of which mate when they are releasably connected e.g. by a bayonet-joint. The opening of the top is partially spanned centrally by a disc, leaving an annular pathway for water around the periphery of the disc. A resilient annular sealing member connected at its outer periphery to the top makes sealing contact with the disc when the base is removed, but when the base is connected to the top the upper periphery of the base raises the sealing member to allow water to fall from the top and be collected in the base.

8 Claims, 3 Drawing Sheets

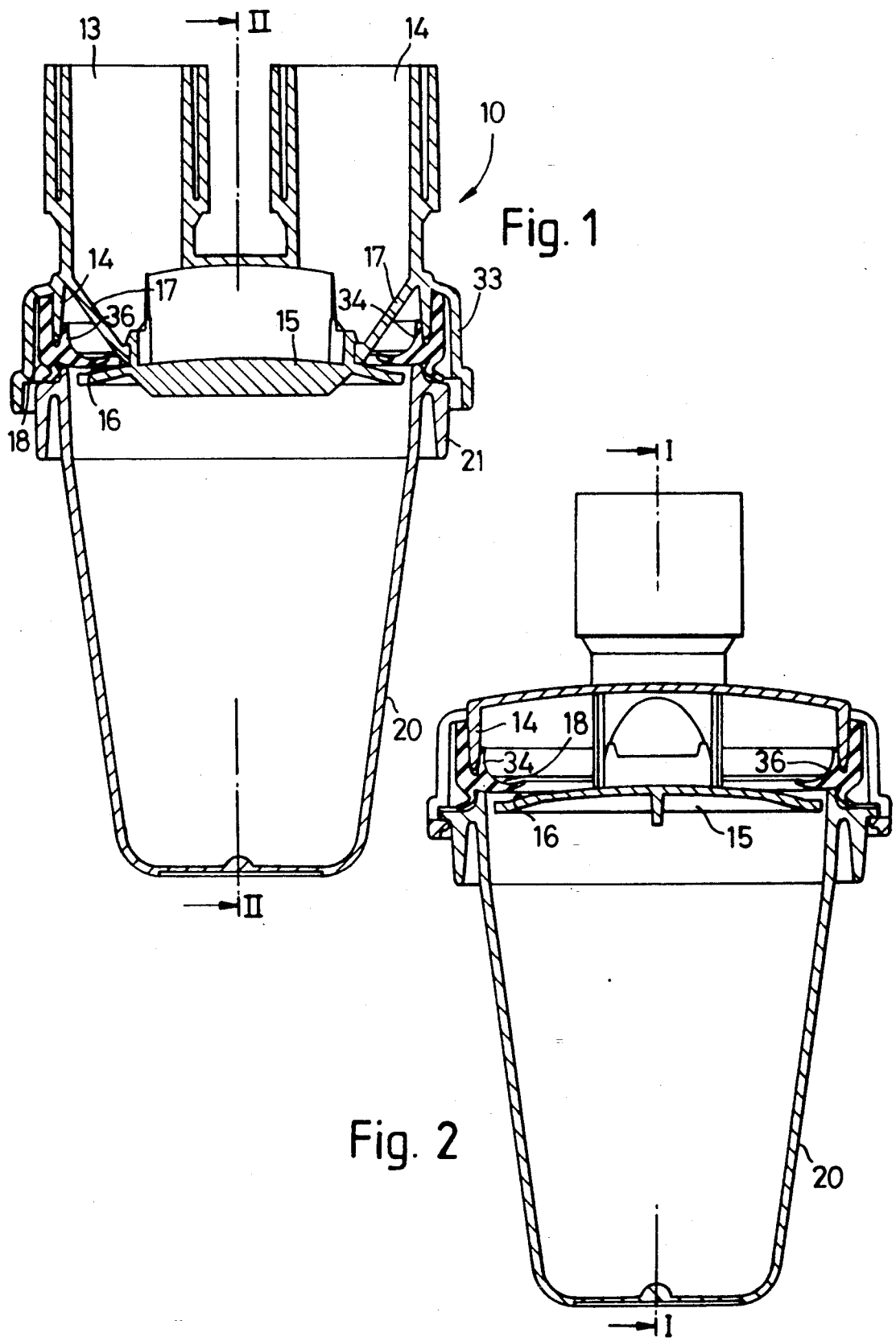

WATER TRAP FOR RESPIRATORY AIRLINE

This invention relates to a water trap for a respiratory airline, and more particularly to a disposable water trap for respiratory and patient ventilation systems used to assist or promote breathing.

In such airlines, used to conduct inhaled and exhaled gases to and from the patient, the problem of condensation and the collection in the airline of moisture which will obstruct it or even tend to drown the patient has been coped with for some years by the inclusion in the airline of a suitably positioned water trap in which the moisture will collect. This is essentially of two parts of which an upper has connections to the airline and the lower, releasably connected to the upper, takes the form of a water collection vessel. Normally the lower part is of a transparent or translucent material so that a nurse or other attendant can see when it is becoming full, disconnect it from the upper part, empty it and replace it.

During this operation—i.e. while the vessel or lower part is disconnected—the upper part must not be open to atmosphere since this would disrupt the treatment and might permit entry into the airline of ambient contaminants such as bacteria. Therefore it has been conventional that the opening of the upper part which normally mates with that of the vessel is controlled by a spring-loaded valve.

The inclusion of a metal spring increases the unit costs, which is undesirable in a disposable item. It is preferable that traps can be produced cheaply enough to avoid the need to sterilise a trap so that it can be used for another patient. On the other hand reduction of unit costs must not be at the expense of reliablity, especially in the ability of the upper part to seal against atmosphere when the lower is disconnected.

Among the objects of the present invention are to provide a water trap in which the use of a metal spring is dispensed with and which may be made cheaply enough to be a disposable item.

In accordance with the present invention there is provided a water trap for a respiratory airline comprising separable upper and lower components of which the upper has inlet and outlet connections to the airline and a downward opening and the lower is in the form of a water collection vessel having an upper opening which, in the connected state of the components, will mate with the opening of the upper component, characterised in that said opening of the upper component is of annular or interrupted-annular configuration and the upper component is provided with one or more resilient sealing members which, in an unstressed condition, will obturate the or each said opening of the upper component, the lower component having an upper periphery shaped so that when the upper and lower components are connected said periphery will displace the or each sealing member to open the or each opening of the upper component whereby a pathway will be provided for water to fall from the upper into the lower component.

In a preferred construction the opening of the upper component has a central obstruction such that a pathway for water around said obstruction is peripheral of said opening of the upper component and of annular or interrupted-annular configuration and releasable connection means between the upper and lower components is located such that when the components are connected the upper periphery of said lower component will extend into said pathway, the upper component being provided with a resilient, annular sealing member secured at its outer periphery to the upper component to span said pathway, the inner periphery of the sealing member being free and adapted sealingly to abut said obstruction in the unstressed condition of the sealing member so as to close said pathway, the arrangement being such that when the upper and lower components are connected said upper periphery of the lower component will displace the sealing member to open said pathway.

Said obstruction may be in the form of a disc held centrally of the opening of the upper component and having a downwardly-sloping upper periphery.

The sealing member is preferably formed intermediate its inner and outer pheripheries with a downwardly and outwardly extending annular projection, the upper periphery of the lower component being arranged to contact the sealing member on the radially inner side of said projection when the components are connected, the lower component being formed below and radially outwardly of said upper periphery thereof with a shoulder which will deform and sealingly engage said projection when the upper and lower components are connected, the arrangement being such that in the unstressed condition of the sealing member the projection is the lowest part of the sealing member and is therefore contacted by the shoulder before said upper periphery contacts the sealing member.

The outer periphery of the sealing member is preferably engaged in a downardly-opening, annular recess on the radially inner side of the outer wall of the upper component, said wall being formed or provided below said recess with releasable connection means engageable with the lower component.

Said recess preferably lies between said outer wall and an inner wall of the upper component and the sealing member preferably has intermediate its ends an upwardly extending annular projection which, in use, will lie adjacent the radially inner side of said inner wall, the arrangement being such that air pressure within the upper component will tend to form an air seal between said upward projection of the sealing member and the inner wall of the upper component.

The sealing member preferably presents a concave annular surface inwardly and upwardly of the upper component between the upper extremity of the upward projection and the inner end of the sealing member.

The outer periphery of the sealing member is preferably engaged in a downardly-opening, annular recess between the inner and outer walls of the upper component, the outer wall being formed or provided below said recess with releasable connection means engageable with the lower component.

Said obtruction may be held in position in said opening of the upper component by tongues extending inwardly and downwardly of the upper component from positions intermediate the upper and lower ends of the latter.

The releasable connection means is preferably a bayonet joint.

Figure 4:
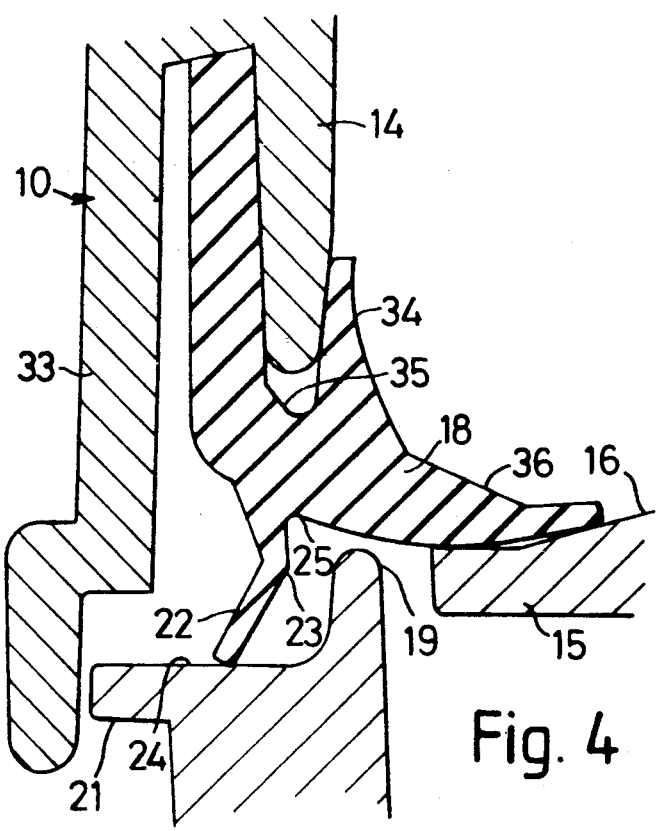
Figure 5:
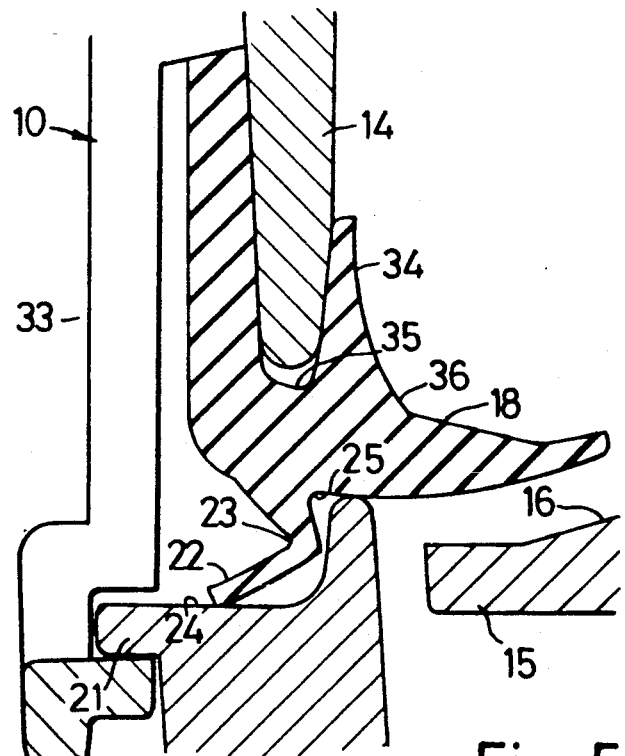

An embodiment of the invention will now be described by way of example with reference to the accompanying drawings, in which:

FIG. 1 is a sectional elevation of a water trap according to the invention shown in the assembled condition and taken on the line I—I of FIG. 2, FIG. 2 is sectional elevation taken on the line II—II of FIG. 1, FIG. 3 is a view similar to FIG. 2 but showing the trap in the dis-assembled condition, and FIGS. 4 and 5 are details on an enlarged scale respectively of FIG. 2 and of FIG. 3

The water trap illustrated in FIGS. 1-3 comprises an upper component or top 10 and a lower component or base 20. The top 10 is formed with connections 13 and 14 whereby it may be included in known manner in an airline by pushing over the connections respective ends of flexible tubes (not shown). The top 10 terminates downwardly in a flared skirt 33 within which an annular wall 14 defines a downwardly-opening recess.

The stepped configuration of the skirt 33 permits optional use of a hook (not shown) to hold the water trap upright. The hook has an upright flange which in use may be inserted into a slot (not shown) in the step of the skirt.

The opening defined by the skirt 33 is spanned except at its periphery by a disc 15 the upper surface of which slopes downwardly at its periphery 16. The disc 15 is held in position centrally of the opening of the top 10 by two tongues 17 which extend downwardly and inwardly from the wall of the top 10 intermediate its upper and lower ends. Trapped in the recess defined by wall 14 is the outer periphery of an annular sealing member 18 of a resilient material such as natural rubber. As most clearly seen in FIG. 4, in the unstressed condition of the sealing member 18 its inner periphery is urged into contact with the top of disc 15, thereby sealing the bottom opening of top 10.

Intermediate its inner and outer peripheries the sealing member 18 has an upward projection 34 whereby an annular groove 35 in the sealing member receives the wall 14. By this arrangement the projection 34 is pressed into contact with the radially inner side of wall 14 and the sealing member presents upwardly and inwardly of the top 10 a concave annular surface 36. By this arrangement any excess air pressure within top 10 will tend to press the projection 34 more closely into sealing enagagement with the wall 14 instead of allowing air to escape between the radially outer side of wall 14 and the main body of the sealing member.

The base 20 is in the form of an upwardly open vessel which is preferably made from a transparent plastics material. Near to but not quite at its upper periphery 19 the base has a flange 21 and this and the skirt 33 have cooperating formations (not shown) providing a bayonet-type releasable connection between the top 10 and base 20. Bayonet connections are well known per se and will not be further described.

As most clearly seen in FIGS. 4 and 5 the sealing member 18 is formed with an annular leg or projection 22 extending downwardly and outwardly therefrom. The projection 22 tapers to a knee-like formation 23 intermediate its ends which facilitates upward flexing of the distal portion of the projection. Between the flange 21 and its upper periphery 19 the base 20 has a shoulder 24 and the arrangement is such that as the base 20 is connected to the top 10 the shoulder 24 will raise the projection 22, forming a seal therewith. Moreover on its radially inner side at the junction with the sealing member 18 the projection 22 defines a notch 25. The upper periphery 19 of the base 20 contacts the sealing member on the radially inner side of this notch (FIG. 5).

As is again most clearly seen in FIGS. 4 and 5, as the upper end of the base 20 is received by the bottom opening of the top 10 and a bayonet connection is made the upper periphery 19 of the base raises the sealing member 18 so that its inner periphery rises from the disc 15. A pathway is thus provided for water to fall from the top 10 to be collected in the base 20. As soon as the base 20 is disconnected from the top 10, however, (FIGS. 3 and 4) for emptying this pathway is sealed as the inner periphery of the sealing member 18 comes back into contact with the upper surface of the disc 15.

The principal purpose of the projection 22 of the sealing member is to provide a temporary seal between the upper and lower parts of the trap before the base 20 is fully connected to the top 10. It will be evident that if the base 20 is approached to the top 10 at a slight angle to the coaxial the upper periphery 19 will tend to lift the sealing member 18 at one point on its circumference instead of uniformly all round. As a result a gap could momentarily appear between the sealing member 18 and disc 15 at a position where the periphery 19 is not in contact with the sealing member and this would permit entry into the water trap of ambient contaminants. To safeguard against this the projection 22, in the unstressed condition of the sealing member 18, extends downward sufficiently to be fully engaged all round by the shoulder 24, providing an air seal between the base 20 and top 10, before the upper periphery 19 contacts the main body of the sealing member 18. This can be ensured because the extent of possible misalignment is, of course, limited by the fact that the base 20 must enter the skirt 33 at the bottom of the top 10.

The water trap described, having a small number of parts, can be produced cheaply and is suitable as a disposable item, i.e. it need not be used for more than one patient. Since it need not be sterilised e.g. by autoclaving for use by a different patient it is possible to use natural rubber for the sealing member 18. The properties of natural rubber are advantageous, but a synthetic such as neoprene would be indicated if the item had to undergo sterilisation.

It will be evident that modification of the above embodiment is possible without departure from the scope of the appended claims. For example the disc 15 may be held in position by means other than the tongues 17. It is not essential that the pathway defined by the raised sealing member should be wholly annular if it is desired that web formations should extend between top 10 and disc 15, and if the pathway is of interrupted-annular configuration so could be the sealing member 18. The projection 22 and notch 25 of the sealing member are not essential. The connection between the top 10 and base 20 may if desired be a screw-threaded one. The connections 13 and 14 of the top 10 may take a variety of forms.

I claim:

1. A water trap for a respiratory airline comprising: an upper component open at a bottom end thereof, a lower component in the form of a water collection vessel releasably connectable to the upper component, inlet and outlet connection means on the upper component for connection to the airline, fixed disc means having a fixed position centrally of said open bottom of the upper component, means defining an upward opening of the lower component, and resilient sealing means in the region of the outer periphery of the upper component which, in an unstressed condition, will seal against said fixed disc means to close the bottom end of the upper component, the lower component having an upper periphery shaped so that when the upper and lower components are connected said upper periphery of said lower component will contact said resilient sealing means first to seal fluidtightly between said upper periphery and said resilient sealing means entirely about said upper periphery and then to displace said resilient sealing means upwardly, thereby to open the bottom of the upper component whereby a pathway will be provided for water to fall from the upper into the lower component only after said upper and lower components are fluidtightly sealed together.

2. A water trap for a respiratory airline comprising: an upper component open at a bottom end thereof, a lower component in the form of a water collection vessel releasably connectable to the upper component, inlet and outlet connection means on the upper component for connection to the airline, fixed disc means having a fixed position centrally of said open bottom of the upper component, means defining an upward opening of the lower component, and an annular resilient sealing member including an annular flap seal secured at its outer periphery in the region of the outer periphery of the upper component at a position such that, in an unstressed condition, said annular flap seal will seal against said fixed disc means thereby to obturate said annular opening of the upper component, the lower component having an upper periphery shaped so that when the upper and lower components are connected said upper periphery of said lower component will press against and first seal fluidtightly between said upper periphery and said sealing member entirely about said upper periphery and then deform said sealing member upwardly to open said annular opening of the upper component whereby a pathway will be provided for water to fall from the upper into the lower component only after said upper and lower components are fluidtightly sealed together.

3. A water trap as claimed in claim 2, wherein disc means has a downwardly-sloping upper periphery.

4. A water trap as claimed in claim 2, wherein the sealing member is formed intermediate its inner and outer pheripheries with a downwardly and outwardly extending annular projection comprising said annular flap seal, the upper periphery of the lower component being arranged to contact the sealing member on the radially inner side of said projection when the components are connected, the lower component being formed below and radially outwardly of said upper periphery thereof with a shoulder which will deform and sealingly engage said projection when the upper and lower components are connected, the arrangement being such that in the unstressed condition of the sealing member the projection is the lowest part of the sealing member and is therefore contacted by the shoulder before said upper periphery contacts the sealing member.

5. A water trap as claimed in claim 2 wherein the outer periphery of the sealing member is engaged in a downwardly-opening, annular recess between the inner and outer walls of the upper component.

6. A water trap as claimed in claim 5, wherein said recess lies between said outer wall and an inner wall of the upper component wherein the sealing member has intermediate its ends an upwardly extending annular projection comprising said annular flap seal which, in use, will lie adjacent the radially inner side of said inner wall, the arrangement being such that air pressure within the upper component will tend to form an air seal between said upward projection of the sealing member and the inner wall of the upper component.

7. A water trap as claimed in claim 6, wherein the sealing member presents a concave annular surface inwardly and upwardly of the upper component between the upper extremity of the upward projection and the inner extremity of the sealing member.

8. A water trap as claimed in claim 2, wherein the disc is held in position by tongues extending inwardly and downwardly of the upper component from positions intermediate the upper and lower ends of the latter.

* * * * *